(12) United States Patent
Reidenberg et al.

(10) Patent No.: US 10,478,640 B2
(45) Date of Patent: Nov. 19, 2019

(54) FIELD STERILIZER AND VASCULAR CONNECTOR KIT

(71) Applicant: CorMedix Inc., Bedminster, NJ (US)

(72) Inventors: Bruce Reidenberg, Rye, NY (US); Antony Pfaffle, Bedminster, NJ (US); Robert DiLuccio, Haymarket, VA (US)

(73) Assignee: CorMedix Inc., Bedminster, NJ (US)

( * ) Notice: Subject to any disclaimer, the term of this patent is extended or adjusted under 35 U.S.C. 154(b) by 235 days.

(21) Appl. No.: 15/471,924

(22) Filed: Mar. 28, 2017

(65) Prior Publication Data

US 2017/0274223 A1 Sep. 28, 2017

Related U.S. Application Data

(60) Provisional application No. 62/313,848, filed on Mar. 28, 2016.

(51) Int. Cl.
*A61L 2/10* (2006.01)
*A61N 5/06* (2006.01)
*A61M 39/16* (2006.01)
*A61M 39/10* (2006.01)

(52) U.S. Cl.
CPC ......... *A61N 5/0624* (2013.01); *A61M 39/105* (2013.01); *A61M 39/162* (2013.01); *A61M 2039/167* (2013.01); *A61M 2205/8206* (2013.01); *A61N 2005/0651* (2013.01); *A61N 2005/0661* (2013.01); *A61N 2005/0666* (2013.01)

(58) Field of Classification Search
CPC ....... A61L 2/10; A61N 5/0624; A61M 39/162
See application file for complete search history.

(56) References Cited

U.S. PATENT DOCUMENTS

| | | |
|---|---|---|
| 5,247,178 A | 9/1993 | Ury et al. |
| 6,485,733 B1 | 11/2002 | Huard et al. |
| 8,790,689 B2 | 7/2014 | Howard et al. |
| 8,840,876 B2 | 9/2014 | Eemeta et al. |

(Continued)

FOREIGN PATENT DOCUMENTS

| | | |
|---|---|---|
| DE | 38 24 647 | 2/1990 |
| EP | 1 718 258 | 3/2009 |
| GB | 2334873 | 9/1999 |

OTHER PUBLICATIONS

Abad, C.L. et al., Catheter-related Bloodstream Infections, Infectious Disease Special Edition, 2011, pp. 84-98.

(Continued)

*Primary Examiner* — Kevin Joyner
(74) *Attorney, Agent, or Firm* — Pandiscio & Pandiscio

(57) ABSTRACT

Placement of a vascular access device (intravenous, intra-arterial and/or intra-osseous vascular access) in a non-sterile environment greatly increases the risk of infection via the vascular access device. This invention provides an approach for accomplishing sterilization of the site where vascular access will be attempted under non-sterile field conditions. In addition, this invention provides a sterile vascular connector pre-loaded with an antimicrobial, e.g., Taurolidine. Use of the vascular connector provides the antimicrobial concurrently with achieving vascular access, which limits the risk of infection despite access placement under non-sterile field conditions.

3 Claims, 4 Drawing Sheets

(56) References Cited

U.S. PATENT DOCUMENTS

| | | | |
|---|---|---|---|
| 2003/0031586 A1 | 2/2003 | Eckhardt et al. | |
| 2008/0275399 A1 | 11/2008 | Gomez Amor | |
| 2011/0081274 A1 | 4/2011 | Packman et al. | |
| 2012/0208802 A1 | 8/2012 | Prosl | |
| 2013/0303972 A1* | 11/2013 | Haytman | A61N 5/0624 604/21 |

OTHER PUBLICATIONS

Allon, M., Prophylaxis Against Dialysis Catheter-Related Bacteremia: A Glimmer of Hope, Am. J. Kidney Dis., vol. 51, No. 2, Feb. 2008, pp. 165-168.

Andjelic, S. et al., Hydrophilic Absorbable Copolyster Exhibiting Zero-Order Drug Release, Pharma. Res., vol. 23, Iss. 4, 2006, pp. 1394-1396.

Betjes, M.G.H. et al., Prevention of dialysis catheter-related sepsis with a citrate-taurolidine-containing lock solution, Nephrol. Dial. Transplant., vol. 19, Iss. 6, 2004, pp. 1546-1551.

Cooper, M.S. et al., Diagnosis and management of hypocalcaemia, BMJ., vol. 336, No. 7656, 2008, pp. 1298-1302.

DiLuccio, R.C. et al., Polyvinyl Alcohol-Methyl Acrylate Copolymers as a Sustained-Release Oral Drug Delivery System, Pharm. Res., vol. 6, Iss. 10, 1989, pp. 844-847.

DiLuccio, R.C. et al., Sustained Release Oral Delivery of Theophylline by use of polyvinyl alcohol-mathyl acrylate polymers, J. Pharm. Sci., vol. 83, Iss. 1, 1994, pp. 104-106.

Donlan, R.M., Biofilm Formation: A Clinically Relevant Microbiological Process, Healthcare Epidemiology, 2001, vol. 33, pp. 1387-1392.

Gong, L. et al., The pharmacokinetics of taurolidine metabolites in healthy volunteers, Journal of Clinical Pharmacology, Jun. 2007, vol. 47, No. 6, pp. 697-703.

Groeger, J.S. et al., Infectious Morbidity Associated with Long-Term Use of Venous Access Devices in Patients with Cancer, Ann. Intern. Med., 1993, vol. 119, pp. 1168-1174.

Jaffer, Y. et al., A Meta-analysis of Hemodialysis Catheter Locking Solutions in the Prevention of Catheter-Related Infection, American Journal of Kidney Diseases, Feb. 2008, vol. 51, No. 2, pp. 233-241.

Johnson, E.N. et al., Infectious Complications of Open Type III Tibial Fractures among Combat Casualties, Clinical Infectious Diseases, 2007, vol. 45, pp. 409-415.

Laplante, K.L. et al., In vitro activity of daptomycin and vancomycin lock solutions on staphylococcal biofilms in a central venous catheter model, Nephrology Dialysis Transplantation, 2007, vol. 22, pp. 2239-2246.

Lin, C. et al., Penetration of Ceftibuten into Middle Ear Fluid, Antimicrobial Agents and Chemotherapy, Jun. 1996, vol. 40, No. 6, pp. 1394-1396.

Lok, C.E. et al., Trisodium citrate 4%—an alternative to heparin capping of haemodialysis catheters, Nephrology Dialysis Transplantation, 2007, vol. 22, pp. 477-483.

Lok, C.E. et al., Hemodialysis Infection Prevention with Polysporin Ointment, J. Am. Soc. Nephrol., 2003, vol. 13, pp. 169-179.

Macrae, J.M. et al., Citrate 4% versus Heparin and the Reduction of Thrombosis Study (CHARTS), Clin. J. Am. Soc. Nephrol., 2008, vol. 3, pp. 369-374.

McIntyre, C.M. et al., Locking of tunneled hemodialysis catheters with gentamicin and heparin, Kidney International, 2004, vol. 66, pp. 801-805.

Murray, C.K. et al., Epidemiology of Infections Associated With Combat-Related Injuries in Iraq and Afghanistan, J. Trauma, 2008, vol. 64, pp. S232-S238.

Phillips, P.L. et al., Antimicrobial dressing efficacy against mature Pseudomonas aeruginosa biofilm on porcine skin explants, Int. Wound J., 2015, vol. 12, pp. 469-483.

Phillips, P.L. et al., Biofilms made easy, Wounds International, May 2010, vol. 1, No. 3, pp. 1-6.

Pichichero, M.E. et al., Clinical and Economic Impact of Enterovirus Illness in Private Pediatric Practice, Pediatrics, Nov. 1998, vol. 102, No. 5, pp. 1126-1134.

Polaschegg, H.-D. et al., Overspill of Catheter Locking Solution: Safety and Efficacy Aspects, ASAIO Journal, 2003, vol. 49, pp. 713-715.

Quarello, F. et al., Prevention of Hemodialysis Catheter-Related Bloodstream Infection Using an Antimicrobial Lock, Blood Purif., 2002, vol. 20, pp. 87-92.

Raiy, B.A. et al., Peripherally inserted central venous catheters in the acute care setting: A safe alternative to high-risk short-term central venous catheters, Am. J. Infect. Control, 2010, vol. 38, pp. 149-153.

Shah, C.B. et al., Antimicrobial Activity of a Novel Catheter Lock Solution, Antimicrobial Agents and Chemotherapy, Jun. 2002, vol. 46, No. 6, pp. 1674-1679.

Simon, A. et al., Taurolidine-citrate lock solution (TauroLock) significantly reduces CVAD-associated grampositive infections in pediatric cancer patients, BMC Infectious Diseases, 2008, vol. 8, No. 102, pp. 1-8.

Sodermann, K. et al., Two Years' Experience with Dialock and CLS (A New Antimicrobial Lock Solution), Blood Purif, 2001, Vo. 19, pp. 251-254.

Solomon, L.R. et al., A Randomized Double-Blind Controlled Trial of Taurolidine-Citrate Catheter Locks for the Prevention of Bacteremia in Patients Treated With Hemodialysis, American Journal of Kidney Diseases, 2010, vol. 55, No. 6, pp. 1060-1068.

Solomon, L.R. et al., Observational Study of Need for Thrombolytic Therapy and Incidence of Bacteremia using Taurolidine-Citrate-Heparin, Taurolidine-Citrate and Heparin Catheter Locks in Patients Treated with Hemodialysis, Seminars in Dialysis, 2012, vol. 25, No. 2, pp. 233-238.

Tauber, M. et al., *Staphylococcus aureus* density or lesional and nonlesional skin is strongly associated with disease severity in atropic dermatitis, J. Allergy Clin. Immunol., Apr. 2016, pp. 1272-1274.

Taylor, C. et al., A new haemodialysis catheter-locking agent reduces infections in haemodialysis patients, Journal of Renal Care, 2008, vol. 34, No. 3, pp. 116-120.

Wolcott, R.D. et al., Biofilm maturity studies indicate sharp debridement opens a time-dependent therapeutic window, Journal of Wound Care, Aug. 2010, vol. 19, No. 8, pp. 320-328.

Yang, Q. et al., Development of a novel ex vivo procine skin explant model for the assessment of mature bacterial biofilms, Wound Repain and Regeneration, 2013, vol. 21, pp. 704-714.

Dittmer et al., A prospective study of central venous hemodialysis catheter colonization and peripheral bacteremia, Clinical Nephrology, 1999, vol. 51, No. 1, Abstract.

\* cited by examiner

FIELD STERILIZER AND VASCULAR CONNECTOR KIT

REFERENCE TO PENDING PRIOR PATENT APPLICATION

This patent application claims benefit of prior U.S. Provisional Patent Application Ser. No. 62/313,848, filed Mar. 28, 2016 by CorMedix Inc. and Bruce Reidenberg et al. for FIELD STERILIZER AND IV CONNECTOR KIT, which patent application is hereby incorporated herein by reference.

FIELD OF THE INVENTION

This invention relates to medical apparatus and methods in general, and more particularly to apparatus and methods for sterile vascular access in the field and prevention of catheter-related infection.

BACKGROUND OF THE INVENTION

1. Field Trauma

In many situations, an individual may require urgent medical care in the field, e.g., in a military combat situation, in a civilian disaster recovery situation, etc. And in many of these situations, it may be necessary to provide immediate access to the vasculature of the patient (e.g., intravenous, intra-arterial and/or intra-osseous vasculature) in primitive field conditions so that appropriate fluids (e.g., saline, plasma, medications, etc.) may be administered to the patient. For the purposes of the present invention, primitive field conditions may be considered to be those where pure water may not be available for cleansing, antiseptic solutions may not be available and/or sterile supplies are limited (such as frequently occurs in military combat situations, civilian disaster recovery situations, etc.).

In these situations, immediate access to the vasculature of the patient is generally achieved by cutting through the skin of the patient and then installing a vascular connector (e.g., a catheter) which provides direct access to the vasculature of the patient. Since infection is a major concern during any procedure which opens the skin and directly accesses the vasculature of a patient, and since infection is a particularly serious concern where such access must be achieved in primitive field conditions, it is desirable to do everything possible to reduce the risk of infection. Among other things, ideally, the skin of the patient should be sterilized prior to incision, and the vascular connector (e.g., the catheter) should be resistant to catheter-related infection.

2. The Desirability of a Field Sterilizer and Vascular Connector Kit

It will be appreciated that where an individual requires urgent medical care in the field, and where such urgent medical care requires immediate access to the vasculature of the patient in primitive field conditions, it would be desirable to provide a pre-packaged kit containing a field sterilizer and a vascular connector, where the vascular connector is resistant to catheter-related infection.

However, certain challenges are encountered when trying to provide a field sterilizer and vascular connector kit.

3. Disinfections Systems

It is known to disinfect water (and other liquids), gases (including air), devices and/or object surfaces, etc. using ultraviolet (UV) radiation and/or disinfectants.

In many situations, it can be highly desirable to disinfect a target medium using UV radiation. For this reason, the present invention is configured to use UV radiation to disinfect the skin of a patient.

A. UV Disinfection Systems in General

Drinking water is commonly treated with UV radiation to disinfect the drinking water—the number of microbes in the water can be reliably and greatly reduced depending on the UV dose which is applied to the drinking water. Exposure to UV radiation causes microorganisms (such as pathogens and other bacteria) to be killed and viruses to be inactivated.

The efficiency of a UV disinfection system is, to a large extent, determined by the UV dose and the homogeneity of the radiation field in which the target medium (e.g., drinking water) is exposed. More particularly, with UV disinfection systems equipped with only a few sources of ultraviolet light, it is difficult to achieve a sufficient homogeneity of the generated UV radiation field for effective disinfecting of the target medium (and, in addition, such systems tend to suffer from high power losses). For disinfecting purposes, it is therefore preferred to provide a highly homogeneous distribution of the UV radiation intensity. In this respect it should be appreciated that a locally-increased UV intensity is generally not detrimental to the disinfecting process, since excess UV intensity typically does not harm the target medium. However, a locally-reduced UV intensity can lead to microorganisms and/or viruses being insufficiently irradiated as they are exposed to the UV disinfection system, thereby undermining the disinfecting process.

In addition to the foregoing, where there are spatial limitations, it may be important for the UV disinfection system to have a compact design (but without compromising system efficiency). In many cases, it may be necessary to reduce the number of UV radiation sources as much as possible for reasons of space (and usually also of cost).

There are two basic approaches for producing UV disinfection systems.

B. Coaxial Geometry Approach for UV Disinfection Systems

A first approach for producing a UV disinfection system uses a coaxial geometry. This coaxial geometry approach is highly compact, but it tends to suffer from radiation homogeneity problems. In a typical configuration, a rod-shaped UV light source is used to create a "UV reactor" in which UV disinfection is carried out. More particularly, the rod-shaped UV light source extends perpendicularly to the plane of the UV disinfection system, within a UV-transparent cover tube, and is arranged so that the target medium (e.g., drinking water) flows around the UV-transparent cover tube which contains the rod-shaped UV light source. Here, the UV light source, covered by the UV-transparent cover tube, is protected from the flowing target media (e.g., drinking water) by the UV-transparent cover tube. Since the radiation intensity of the UV light source decreases exponentially with distance, and since the radiation intensity of the UV light source is also weakened by absorption in the target medium, this results in a non-homogeneous radiation field. Strongly-non-homogeneous radiation fields result in a strong deviation of the UV dosage delivered across the area being treated. If there is a strongly-non-homogeneous radiation field, there will likely be areas in which existing microorganisms and viruses in the target medium cannot be irradiated sufficiently due to the low UV radiation intensity. The disinfection performance is therefore insufficient.

C. Elliptical Reflectors Approach for UV Disinfection Systems

A second approach for producing a UV disinfection system uses elliptical reflectors to create the UV reactor. More particularly, in these UV disinfection systems, UV light sources are arranged outside of the UV reactor (i.e., the UV radiation zone) and then the UV radiation is transmitted to the UV reactor via an arrangement of elliptical reflectors. These elliptical reflectors produce a relatively homogeneous radiation field in the UV reactor, but they generally require a relatively large space to produce the relatively homogenous radiation field. For this reason, UV disinfection systems using elliptical reflectors are generally not suitable for applications which must be compact.

D. Deficiencies of UV Disinfection Systems

Therefore, current UV disinfection systems generally provide either (i) a compact design but insufficient radiation homogeneity (e.g., UV disinfection systems using a coaxial geometry approach); or (ii) a high radiation homogeneity but require a large installation space (e.g., UV disinfection systems using elliptical reflectors).

3. Catheter-Related Infection

It is well known that vascular connectors (e.g., catheters) are highly susceptible to catheter-related infection. The source of the infection can be microorganisms and/or viruses present at the time of the installation of the vascular connector (e.g., catheter), or the source of the infection can be microorganisms and/or viruses which are introduced to the vascular connector (e.g., the catheter) after installation of the vascular connector (e.g., catheter). In either case, such infection is always of significant concern due to the direct access of the vascular connector (e.g., the catheter) to the vasculature of the patient.

4. Primary Object of the Invention

Accordingly, the primary object of the present invention is to provide a pre-packaged kit for use in rapidly accessing the vasculature of a patient in primitive field conditions, wherein the pre-packaged kit contains a field sterilizer and a vascular connector, and wherein the vascular connector is resistant to catheter-related infection.

SUMMARY OF THE INVENTION

The present invention comprises the provision and use of a novel field sterilizer and vascular connector kit which comprises (i) a UV sterilizer, and (ii) a vascular connector pre-filled with an antimicrobial solution that is safe for injection into the patient. The UV sterilizer is compact in size and comprises at least one UV light source disposed in a reflective chamber so that UV sterilization of a skin surface can be achieved without threatening the vision of a caregiver who is conducting the treatment. The UV sterilization of the patient's skin is then followed by vascular access using the vascular connector (which is preferably in the form of a 3-way hub connector), wherein the vascular connector comprises a supply of the antimicrobial Taurolidine to prevent future catheter-related infection.

In one preferred form of the invention, there is provided a field sterilizer and vascular connector kit comprising:

a UV sterilizer comprising a UV light source and a power source, wherein the UV light source and the power source are configured so as to provide a UV dosage to the skin of a patient which is sufficient to effectively disinfect the skin of the patient without burning the skin of the patient; and a vascular connector releasably mounted to the UV sterilizer, wherein the vascular connector contains a supply of an antimicrobial.

In another preferred form of the invention, there is provided a method for providing sterile access to the vasculature of a patient, the method comprising:

providing a field sterilizer and vascular connector kit comprising:

a UV sterilizer comprising a UV light source and a power source, wherein the UV light source and the power source are configured so as to provide a UV dosage to the skin of a patient which is sufficient to effectively disinfect the skin of the patient without burning the skin of the patient; and a vascular connector releasably mounted to the UV sterilizer, wherein the vascular connector contains a supply of an antimicrobial;

using the UV sterilizer to disinfect the skin of the patient; and using the vascular connector to provide access to the vasculature of the patient.

In another preferred form of the invention, there is provided a UV sterilizer comprising a UV light source, a portable power source and a reflective chamber, the UV light source being positioned within the reflective chamber so that the UV light source can effect UV sterilization of a skin surface without light leakage.

In another preferred form of the invention, there is provided a vascular connector comprising a hollow body pre-filled with a solution comprising Taurolidine.

In another preferred form of the invention, there is provided a method for sterilizing a skin surface, the method comprising:

providing a UV sterilizer comprising a UV light source, a portable power source and a reflective chamber, the UV light source being positioned within the reflective chamber so that the UV light source can effect UV sterilization of the skin surface without light leakage; and using the UV sterilizer to disinfect the skin surface.

In another preferred form of the invention, there is provided a method for providing sterile access to the vasculature of a patient, the method comprising:

providing a vascular connector comprising a hollow body pre-filled with a solution comprising Taurolidine; and using the vascular connector to provide access to the vasculature of the patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
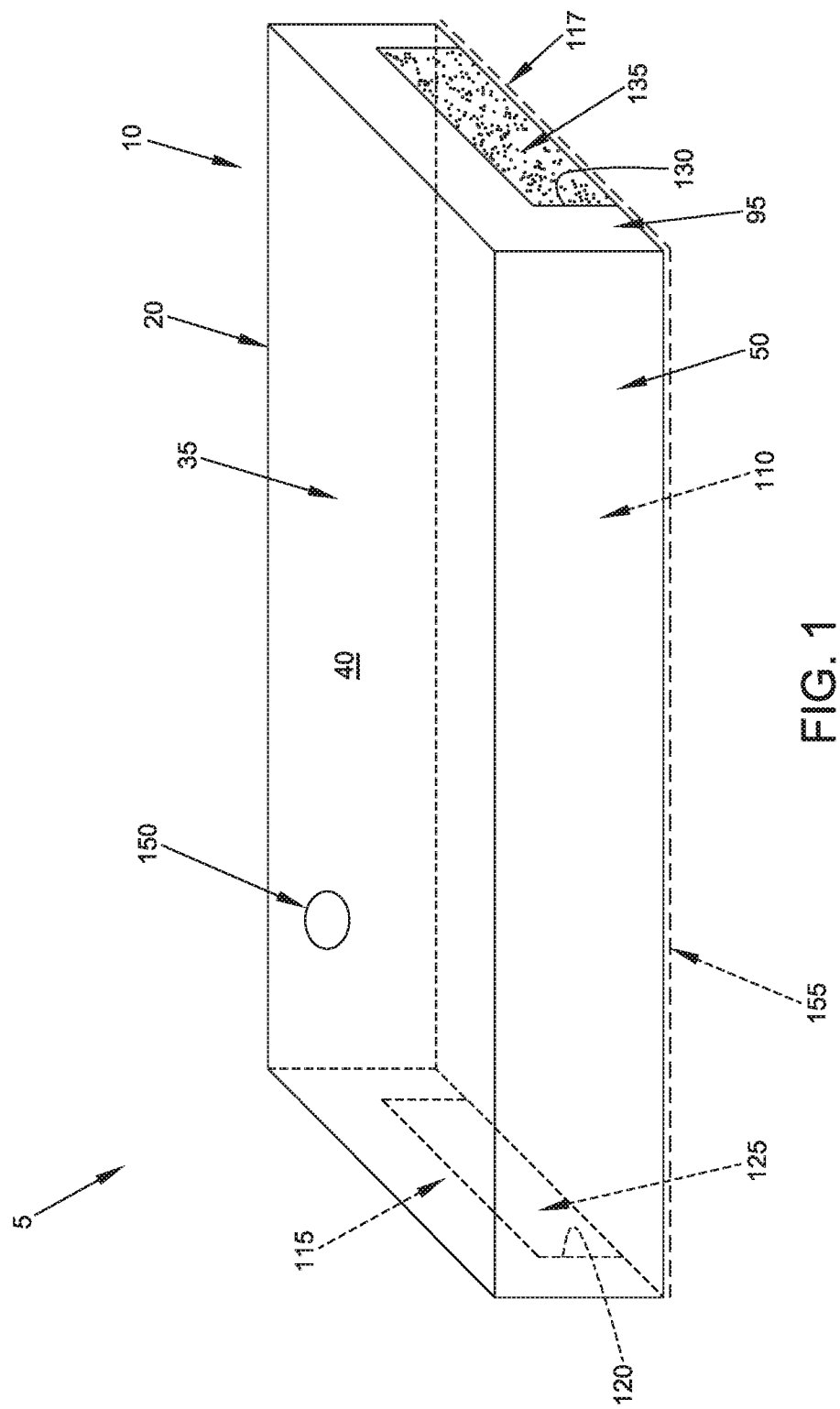
FIG. 1 is a schematic view showing the exterior of a field sterilizer and vascular connector kit formed in accordance with the present invention.
Figure 2:
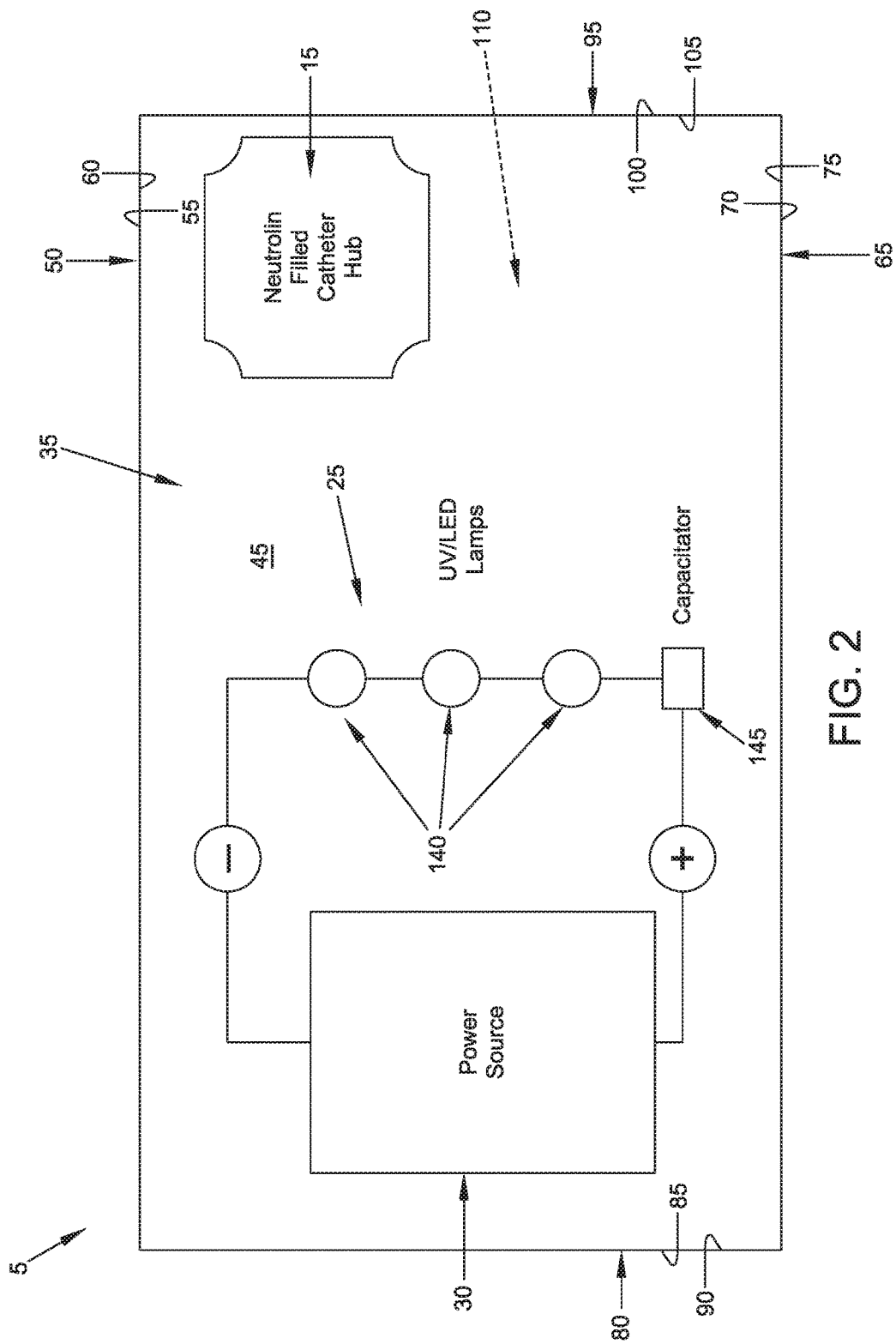
FIG. 2 is a schematic view showing the underside of the field sterilizer and vascular connector kit shown in FIG. 1.
Figure 3:
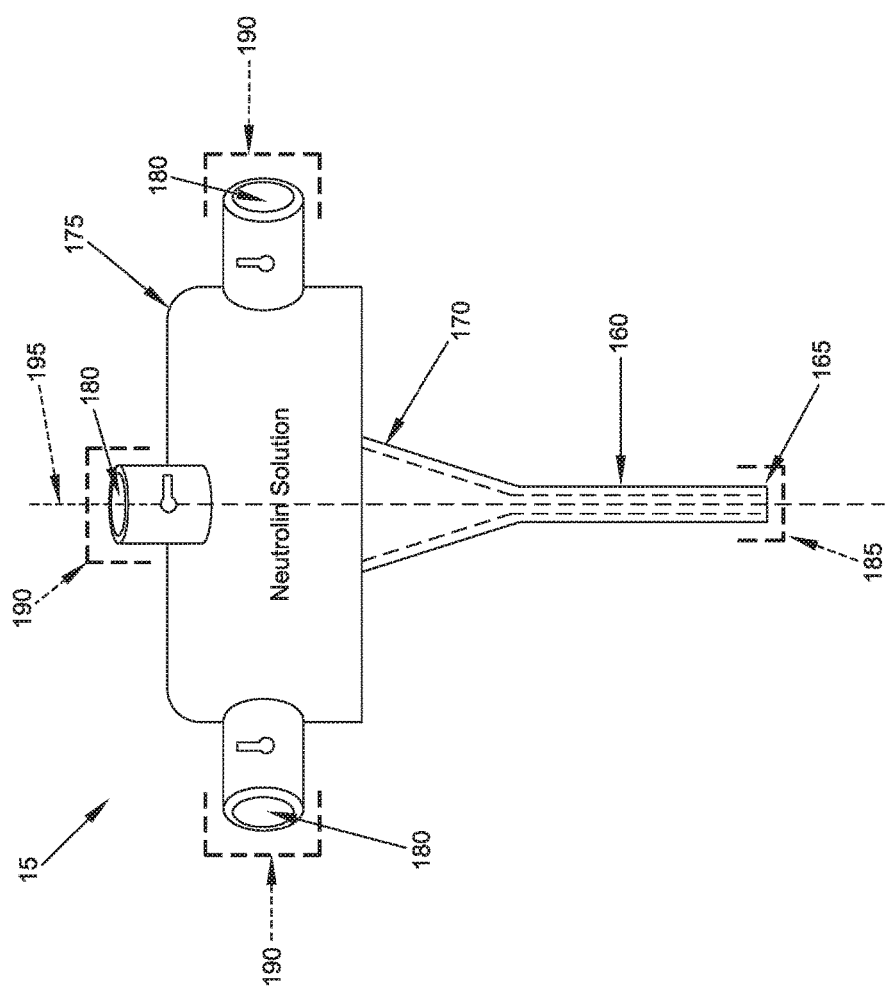
FIG. 3 is a schematic view showing details of the vascular connector which is mounted to the underside of the field sterilizer and vascular connector kit shown in FIG. 1.

In accordance with the present invention, and looking now at FIGS. 1-3, there is provided a novel UV sterilizer and vascular connector kit 5 which may be used for sterilizing a patient's skin and then providing sterile vascular access to the vasculature of a patient. UV sterilizer and vascular connector kit 5 generally comprises (i) a UV sterilizer 10, and (ii) a vascular connector 15 with enhanced antimicrobial action.

1. UV Sterilizer 10

UV sterilizer 10 is compact in size and generally comprises (i) a housing 20, (ii) a UV light source 25, and (iii) a power source 30 for powering UV light source 25. See FIGS. 1 and 2.

More particularly, in one preferred form of the invention, housing 20 generally comprises a panel 35 having a top surface 40 and a bottom surface 45; a front wall 50 having an outside surface 55 and an inside surface 60; a back wall 65 having an outside surface 70 and an inside surface 75; a left side wall 80 having an outside surface 85 and an inside surface 90; and a right side wall 95 having an outside surface 100 and an inside surface 105. Panel 35, front wall 50, back wall 65, left side wall 80 and right side wall 95 cooperate with one another as shown in FIGS. 1 and 2 so as to form a concave recess 110 on the underside of housing 20.

Housing 20 is compact in size, e.g., it is preferably approximately 10 cm long×6 cm wide×3 cm high.

Bottom surface 45 of panel 35, inside surface 60 of front wall 50, inside surface 75 of back wall 65, inside surface 90 of left side wall 80 and inside surface 105 of right side wall 95 preferably all comprise a UV light-reflecting material (e.g., a high reflectance metal), such that concave recess 110 constitutes a UV light-reflecting chamber. In one preferred form of the invention, panel 35, front wall 50, back wall 65, left side wall 80 and right side wall 95 are all formed out of a material which is UV light-reflecting. In another preferred form of the invention, panel 35, front wall 50, back wall 65, left side wall 80 and right side wall 95 are formed out of a material which is not UV light-reflecting, and they are all coated with a material which is UV light-reflecting.

In one preferred form of the invention, left side wall 80 also comprises a light baffle 115 and right side wall 95 comprises a light baffle 117. More particularly, left side wall 80 comprises an opening 120 which is normally closed off by a UV-opaque structure 125. However, UV-opaque structure 125 is constructed so that it may be pushed aside when desired (e.g., UV-opaque structure 125 may comprise a curtain, a plurality of bristles, etc.). Similarly, right side wall 95 comprises an opening 130 which is normally closed off by a UV-opaque structure 135. However, UV-opaque structure 135 is constructed so that it may be pushed aside when desired (e.g., UV-opaque structure 135 may comprise a curtain, a plurality of bristles, etc.).

In one preferred form of the invention, housing 20 may comprise a frame carrying one or more Mylar® (or other plastic) sheets, e.g., so that the housing can be folded along its long axis to provide a more compact shape for packaging. In another preferred form of the invention, housing 20 may comprise a plurality of self-standing Mylar® (or other plastic) sheets, etc.

UV light source 25 and power source 30 (for powering UV light source 25) are mounted to bottom surface 45 of panel 35 so that UV light may be directed on a skin surface opposing bottom surface 45 of panel 35. UV light source 25 and power source 30 are configured so as to provide a UV dosage to the skin of the patient which is sufficient to effectively disinfect the skin of the patient without burning the skin of the patient. UV light source 25 and power source 30 are also configured so as to provide the disinfecting UV dosage in a relatively short period of time, e.g., 30-60 seconds. UV light source 25 preferably comprises a plurality of UV light-emitting diodes (LEDs) 140 of the sort well known in the art of UV disinfection systems. Power source 30 comprises an appropriate battery (e.g., a 9V battery) for powering UV light source 25, and may include a capacitor 145 and various control circuitry (including an on/off button 150), etc. of the sort well known in the art of electrical power systems.

Vascular connector 15 is releasably mounted in concave recess 110 of housing 20 (e.g., vascular connector 15 is mounted to bottom surface 45 of panel 35) so that vascular connector 15 is readily available to be installed in a patient after UV sterilizer 10 has been used to sterilize the skin of a patient. In one preferred from of the invention, vascular connector 15 is releasably secured to bottom surface 45 of panel 35 by mounting vascular connector 15 to bottom surface 45 of panel 35 with easily-released clips of the sort well known in the art of packaging, or with other releasable securement mechanisms of the sort well known in the art of packaging.

Concave recess 110 of housing 20 is preferably closed off with a sterile seal 155 which is removed in the field at the time of use. By way of example but not limitation, sterile seal 155 may comprise a pull sheet which is releasably secured to front wall 50, back wall 65, left side wall 80 and right side wall 95. As a result of this construction, the various components housed in concave recess 110 (e.g., vascular connector 15, UV light source 25 and power source 30) may all be maintained in a sterile condition until the time of use.

2. Vascular Connector 15

Vascular connector 15 preferably comprises a standard 3-way stopcock-controlled connector (see FIG. 3). More particularly, vascular connector 15 preferably comprises a hollow tube 160 having a distal end 165 and a proximal end 170. Proximal end 170 is in fluid communication with a hollow housing 175. Hollow housing 175 preferably comprises 3 ports 180 which are in fluid communication with hollow housing 175. Ports 180 are preferably stopcock-controlled ports. As is well known in the art, vascular connector 15 is intended to have its distal end 165 positioned within the vasculature of a patient and ports 180 used to deliver appropriate fluids (e.g., saline, plasma, medications, etc.) to the vasculature of the patient.

In accordance with the present invention, vascular connector 15 is pre-filled with an antimicrobial which is safe to be injected into a patient. In the preferred form of the invention, the antimicrobial is Taurolidine, and the Taurolidine is in solution form (e.g., such as the Taurolidine catheter lock solution sold by CorMedix Inc. of Bridgewater, N.J. under the trade name Neutrolin®). The Taurolidine is contained within hollow tube 160 and hollow housing 175 of vascular connector 15 by a removable cap 185 positioned on distal end 165 of hollow tube 160 and by setting the stopcocks of ports 180 in their closed positions. Additionally, if desired, removable caps 190 may be positioned on the 3 ports 180. Alternatively, removable cap 185 and/or removable caps 190 may be replaced by easily-punctured diaphragms of the sort well known in the art.

If desired, a vascular access guidewire 195 of the sort well known in the art of catheter access may be included with, but not disposed within, vascular connector 15.

3. Use

1. The site of the intended vascular access is cleaned of debris—note that there is no requirement of alcohol or betadine or other antiseptics, the site may be cleaned with local impure water, or even spit or urine, or simply brushed off with a cloth or by hand.

2. Housing 20 of UV sterilizer 10 is unfolded (if it was packaged in a folded condition) and then sterile seal 155 is removed from the bottom of housing 20 of UV sterilizer 10, thereby exposing concave recess 110 of housing 20.

3. Power source 30 is connected to UV light source 25 (if UV sterilizer 10 was packaged with power source 30 disconnected from UV light source 25).

4. UV sterilizer 10 is placed against the skin of the patient at the site of the intended vascular access so that UV light source 25 is directed toward the site of the intended vascular access. UV sterilizer 10 makes a firm connection with the anatomy of the patient (i.e., the "rim" of concave recess 110 makes a firm connection with the skin of the patient) so as to avoid any light leakage, with UV opaque structures 125 and 135 closing off openings 120 and 130 of housing 20, respectively. Note that if UV sterilizer 10 is being placed on a limb of the patient, openings 120 and 130 in left side wall 80 and right side wall 95, respectively, of housing 20 can receive a portion of the patient's limb so that UV sterilizer 10 will seat in a stable manner on the limb. As this occurs, UV-opaque structures 125 and 135 may be pushed aside to the extent required to accommodate the anatomy of the patient, however, UV-opaque structures 125 and 135 will prevent UV light leakage through light baffles 115 and 117, respectively.

5. UV sterilizer 10 is activated (e.g., by pushing on/off button 150). When this occurs, UV light is directed onto the skin of the patient, whereby to sterilize the skin of the patient, without threatening the vision of the caregiver who is conducting the treatment (and without allowing light to escape and reveal the location of the patient, which may be important in military applications).

6. When UV sterilization is completed, UV sterilizer 10 is turned off (e.g., by pushing on/off button 150 again), UV sterilizer 10 is removed from the site of the vascular access, and vascular connector 15 is removed from bottom surface 45 of panel 35.

7. Removable cap 185 is removed from distal end 165 of vascular connector 15, distal end 165 of vascular connector 15 is advanced through the now-sterile skin surface, and distal end 165 of vascular connector 15 introduced into the vasculature of the patient. Note that the Taurolidine contained within the hollow body of vascular connector 15 provides antimicrobial action to limit catheter-related infection. Note that, if desired, vascular access guidewire 195 may be used to assist in the deployment of vascular connector 15, in which case vascular access guidewire 195 is first passed through the skin of the patient and into the vasculature of the patient, and then vascular connector 15 is passed over vascular access guidewire 195 and through the skin of the patient and into the vasculature of the patient (note also that where the proximalmost port 180 of vascular connector 15 comprises a stopcock and/or a cap 190, the stopcock will need to be opened and/or the cap 190 will need to be removed in order for the vascular connector 15 to be loaded over vascular access guidewire 195). Then vascular access guidewire 195 is withdrawn from vascular connector 15.

8. Once vascular connector 15 has been deployed in the patient, one or more of ports 180 may be connected to an appropriate fluid source for delivery of appropriate fluids (e.g., saline, plasma, medications, etc.) to the vasculature of the patient. Note that the Taurolidine contained within the body of vascular connector 15 may be pushed safely into the vasculature of the patient ahead of the fluid which is to be delivered to the patient. Alternatively, some or all of the Taurolidine contained within the body of vascular connector 15 may be removed from the body of the vascular connector 15 via one or more of the ports 180 prior to introducing a desired fluid into the vasculature of the patient.

9. Once vascular connector 15 has been deployed in the vasculature of the patient, UV sterilizer 10 may be used to sterilize another tissue surface (e.g., of the same patient or of another patient).

4. Alternative Vascular Connector 15A

Figure 4:
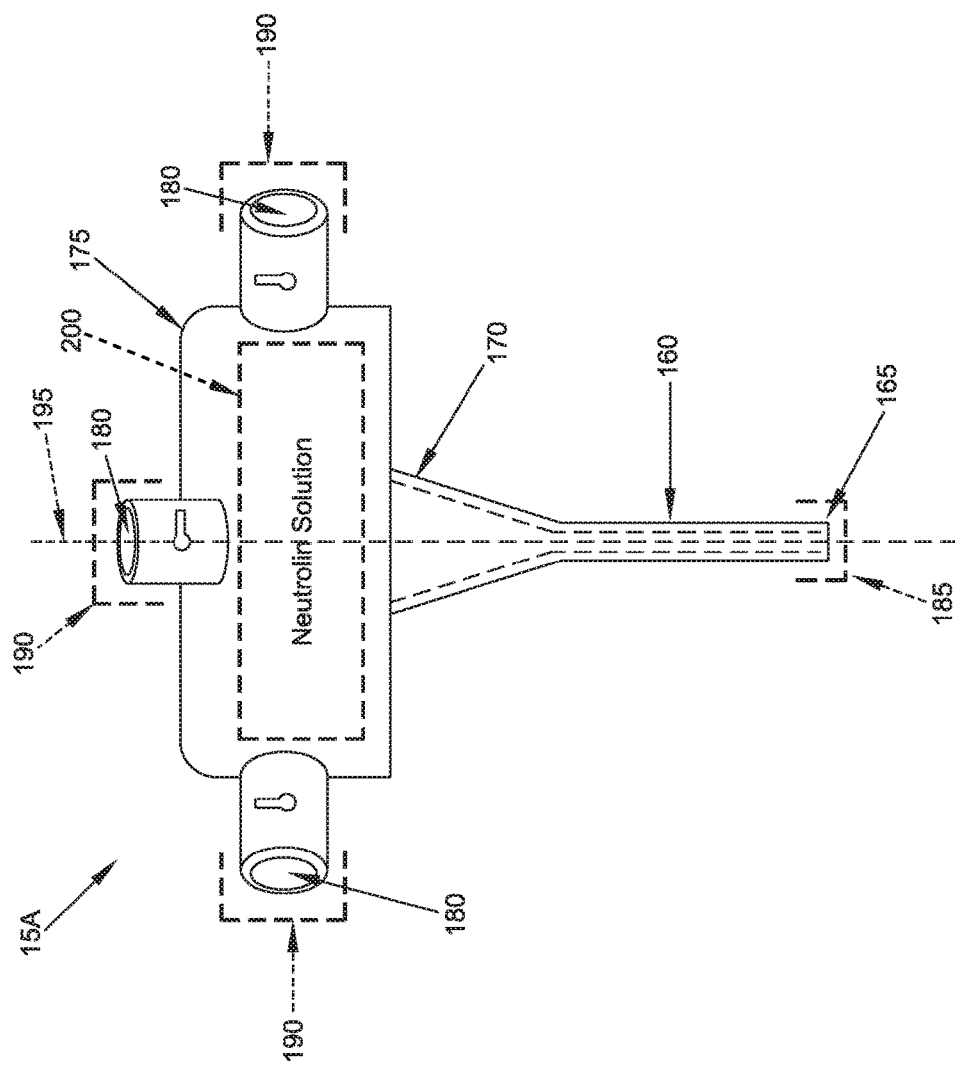
FIG. 4 is a schematic view of another vascular connector which may be used with the field sterilizer and vascular connector kit of FIG. 1.

In an alternative form of the invention, a vascular connector 15A (FIG. 4) may be provided. Vascular connector 15A is substantially the same as vascular connector 15 described above, except that a porous disc 200 may be disposed within hollow housing 175 of vascular connector 15A. Porous disc 200 is formed out of a material which is capable of containing and releasing an antimicrobial (e.g., porous disc 200 may be in the form of a hydrogel web or mesh). Porous disc 200 is impregnated with an antimicrobial. In the preferred form of the invention, the antimicrobial is a solution of Taurolidine, such as the Neutrolin®-heparin 100 unit catheter lock solution sold by CorMedix Inc., which is a Taurolidine solution containing low-dose heparin (heparin can be helpful to prevent clotting in vascular connector 15A, but low-dose heparin may be preferred since the patient may be bleeding in the field). If desired, the remaining spaces within the interior of vascular connector 15A (i.e., the spaces not taken up with porous disc 200) may also be filled with the Taurolidine solution.

In addition, the ante-chamber of each port 180 may be filled with a gel formulation which must be removed or pierced in order to enable flow through that port. In this way, there are two lines of defense to prevent infection and biofilm.

Furthermore, a port 180 may have a length of intravenous tubing pre-connected to that port and pre-filled with an antimicrobial, e.g., a catheter lock solution comprising Taurolidine such as that sold by CorMedix Inc.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. A field sterilizer and vascular connector kit comprising:
a UV sterilizer comprising (i) a UV light source and a power source, wherein the UV light source and the power source are configured so as to provide a UV dosage to the skin of a patient which is sufficient to effectively disinfect the skin of the patient without burning the skin of the patient, and (ii) a housing defining a reflective chamber, wherein the UV light source is disposed in the reflective chamber; and
a vascular connector releasably mounted to the UV sterilizer, wherein the vascular connector contains a supply of an antimicrobial, and wherein the vascular connector is releasably mounted within the reflective chamber.

2. A field sterilizer and vascular connector kit according to claim 1 wherein the reflective chamber is closed off by a removable sterile seal.

3. A field sterilizer and vascular connector kit comprising:
- a UV sterilizer comprising a UV light source and a power source, wherein the UV light source and the power source are configured so as to provide a UV dosage to the skin of a patient which is sufficient to effectively disinfect the skin of the patient without burning the skin of the patient; and
- a vascular connector releasably mounted to the UV sterilizer, wherein the vascular connector contains a supply of an antimicrobial, and wherein the vascular connector comprises a body having a hollow interior, a distal opening and at least one proximal opening, and further wherein the distal opening and the at least one proximal opening are selectively sealed so as to releasably contain the supply of the antimicrobial within the hollow interior of the body.

* * * * *